United States Patent [19]

Lau et al.

[11] Patent Number: 5,614,357
[45] Date of Patent: Mar. 25, 1997

[54] PHOTOGRAPHIC ELEMENT CONTAINING A PARTICULAR CYAN COUPLER BEARING A SULFONYL CONTAINING BALLAST

[75] Inventors: Philip T. S. Lau; Stanley W. Cowan, both of Rochester, N.Y.

[73] Assignee: Eastman Kodak Company, Rochester, N.Y.

[21] Appl. No.: 661,234

[22] Filed: Jun. 10, 1996

[51] Int. Cl.⁶ .................................................... G03C 7/34
[52] U.S. Cl. .................................... 430/552; 430/553
[58] Field of Search ................................. 430/556, 553

[56] References Cited

U.S. PATENT DOCUMENTS 5,399,467  3/1995  Krishnamurthy et al. ............ 430/552

FOREIGN PATENT DOCUMENTS 4000954  1/1989  Japan ..................................... 430/553

Primary Examiner—Lee C. Wright
Attorney, Agent, or Firm—Arthur E. Kluegel

[57] ABSTRACT

The invention provides a photographic element comprising a light sensitive silver halide emulsion layer having associated therewith a cyan coupler represented by formula (I):

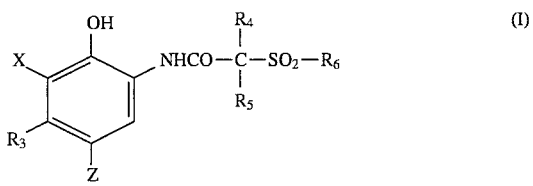

wherein:
  $R_3$ represents an alkyl group of 2 to 15 carbon atoms;
  $R_4$ and $R_5$ each independently represents a hydrogen atom, an alkyl group or an aryl group;
  $R_6$ represents an alkyl or aryl group;
  X represents a halogen atom; and
  Z represents a hydrogen atom or a group capable of being split off by oxidized color developer.

15 Claims, 1 Drawing Sheet

FIG. 1

PHOTOGRAPHIC ELEMENT CONTAINING A PARTICULAR CYAN COUPLER BEARING A SULFONYL CONTAINING BALLAST

FIELD OF THE INVENTION

The present invention relates to a photographic element containing a silver halide emulsion layer having associated therewith a phenolic cyan coupler having a sulfonyl containing ballast.

BACKGROUND OF THE INVENTION

A typical photographic element contains multiple layers of light-sensitive photographic silver halide emulsions with one or more of these layers being spectrally sensitized to each of blue light, green light and red light. The blue, green and red light-sensitive layers typically contain yellow, magenta, and cyan dye-forming couplers, respectively. To form a color photographic image, the color photographic material is exposed imagewise and processed in a color developer bath containing an aromatic primary amine color developing agent. Image dyes are formed by the coupling reaction of these couplers with the oxidized product of the color developing agent.

Generally, image couplers are selected according to their ability to couple efficiently with oxidized color developer, thus minimizing the necessary amounts of coupler and silver halide emulsion in the photographic element; to provide image dyes whose hues are appropriate for the particular photographic application in which they are to be used; to provide image dyes whose absorption spectra have low unwanted side absorptions and thus lead to good color reproduction; to provide image dyes with good stability to heat, light, and ferrous ions which are present in the bleaching solution; and to provide good physical and chemical properties such as good solubility in coupler solvents, and good dispersibility in gelatin.

In the case of color negative image capture films, the absorption maximum of the image dye should generally be 680 nm or longer, preferably 690 nm or longer, and it should have as little absorption in the green region of the spectrum as possible.

The couplers commonly used to form cyan image dyes in color photographic films and papers are generally of three types, namely, the 1-hydroxy-2-naphthamides represented by formula (A) and described in U.S. Pat. Nos. 2,313,138, 3,002,836, 4,208,210, 5,283,163, 5,380,638, 5,457,008, and 5,476,757; the 2,5-diacylaminophenols and 2-arylureido-5-acylaminophenols represented by formula (B) and described in U.S. Pat. Nos. 2,369,929, 2,895,826, 3,466,622, 3,758, 308, 3,864,366, 3,880,661, 3,996,253, 4,333,999, 4,451,559, 4,465,766, and 4,554,244; and the 2-acylamino-5-alkylphenols represented by formula (C) and described in U.S. Pat. Nos. 2,367,531, 2,369,929, 2,423,730, 2,801,171, 3,772, 002, 3,998,642, and 4,560,630. These types of couplers can be used either by being incorporated in the photographic silver halide emulsion layers or externally in the processing baths. In the former case the couplers must have ballast substituents built into the molecule to prevent the couplers from migrating from one layer into another.

In each of the formulas (A) and (C), $R_1$ represents an alkyl or aryl group; in (B), $R_1$ represents an alkyl, aryl or arylamino group. In (A), (B), and (C), Z represents a hydrogen atom or a group which is split off during the coupling reaction ("coupling-off group"). In (B), $R_2$ represents an alkyl or aryl group, usually an alkyl group substituted at the alpha position by an aryloxy group. In (C), $R_3$ represents an alkyl group, usually methyl or ethyl, X represents a halogen atom, usually chlorine or fluorine, and X and Z are usually (but not necessarily) the same.

Although these couplers have been used extensively in color photographic film and paper products, the dyes derived from each of the three types suffer from various deficiencies that make them unsatisfactory for use in color photographic color negative films.

Naphthol cyan couplers of formula (A), in particular the cyan couplers of formula (D), are used primarily in color photographic negative films. In formula (D), Z is usually a hydrogen atom, a chlorine atom, a fluorine atom, an alkoxy group, or an aryloxy group.

The image dyes derived from the couplers of formula (A) have relatively long absorption maxima, generally in the range of 690–705 nm. However, the image dyes derived from these couplers have poor stability to heat and humidity, and to ferrous ions that are present in the bleaching solution.

In recent years the preferred cyan couplers for use in color negative films are the 2,5-diacylaminophenols of formula (B), in particular the 2-arylureido-5-acylaminophenols of formula (E), described in U.S. Pat. No. 4,333,999. In formula (E) Z is usually a hydrogen atom, a chlorine atom, a fluorine atom, or an aryloxy group.

The image dyes derived from the couplers of formula (E) have long absorption maxima, generally in the range of 685–700 nm, which is ideally suited for use in color negative films. Furthermore, the image dyes have excellent stability to heat and humidity and to ferrous ions. While these are substantial improvements over the couplers of formula (A), these couplers have some drawbacks. One serious drawback is that the image dyes derived from them have broad absorption spectra with too much undesirable absorption in the green region. Furthermore, they suffer from poor solubility in common coupler solvents, resulting in coupler crystallization during storage of the dispersions or of the photographic elements in which they are coated. A still further drawback is that they are expensive to manufacture.

The 2-acylaminophenol cyan couplers of formula (C), in particular the couplers of formula (F), are widely used in color photographic papers and color print films. In formula (F) $R_3$ may be methyl or ethyl.

The couplers of formula (F) are among the least expensive of all cyan couplers to manufacture. They have good solubility in common coupler solvents and good dispersibility, resulting in dispersions with excellent keeping stability and photographic elements that are free of coupler crystallization. These couplers have excellent coupling efficiency. Furthermore, the image dyes derived from these cyan couplers have good stability, particularly ti light. The image dyes have absorption maxima around 630–670 nm. While these properties make them well suited for use in color photographic papers and color print films, their short absorption maxima make them unsuited for use in color negative films.

It is a problem to be solved to provide a photographic element that enables the formation during processing of a cyan dye having a maximum absorbance of at least 680 nm and having a sharp cutting spectrum on the short wavelength side of the maximum.

SUMMARY OF THE INVENTION

The invention provides a photographic element comprising a light sensitive silver halide emulsion layer having associated therewith a cyan coupler represented by formula (I):

wherein:

$R_3$ represents an alkyl group of 2 to 15 carbon atoms;

$R_4$ and $R_5$ each independently represents a hydrogen atom, an alkyl group or an aryl group;

$R_6$ represents an alkyl or aryl group;

X represents a halogen atom; and

Z represents a hydrogen atom or a group capable of being split off by oxidized color developer.

The invention also encompasses the dye formed from the coupler of the invention, and an imaging process employing the element of the invention.

The element of the invention enables the formation during processing of a cyan dye having a maximum absorbance of at least 680 nm and having a sharp cutting spectrum on the short wavelength side of the maximum.

DETAILED DESCRIPTION OF THE INVENTION

The couplers of formula (I) are more particularly described as follows.

In formula (I), $R_3$ represents an alkyl group of 2 to 15 carbon atoms, such as an ethyl or propyl group, and most preferably an ethyl group. $R_4$ and $R_5$ independently represent a hydrogen atom, a linear or branched alkyl group of 1 to 30 carbon atoms, or an aryl group. Suitably, $R_4$ and $R_5$ each represents a hydrogen atom or a linear or branched alkyl group such as methyl, ethyl, isopropyl, t-butyl, or dodecyl, and $R_4$ and $R_5$ together contain 1 to 30 carbon atoms.

$R_6$ represents a linear or branched, saturated or unsaturated alkyl group having preferably 1 to 20 carbon atoms, such as methyl, propyl or dodecyl group; or an aryl group such as a phenyl group or a naphthyl group having typically 6 to 30 carbon atoms, which may be substituted by, for example, 1 or more alkyl groups, aryl groups, halogen atoms, cyano groups, carbonyl groups, carbonamido groups, sulfonamido groups, carboxy groups, sulfo groups, alkoxy groups, aryloxy groups, alkylthio groups, arylthio groups, alkylsulfonyl groups or arylsulfonyl groups. X represents a halogen atom, preferably a chlorine or fluorine atom.

Z represents a hydrogen atom or a group which can be split off by the reaction of the coupler with an oxidized color developing agent, known in the art as a "coupling-off group." Such groups can determine the chemical equivalency of a coupler, i.e., whether it is a 2-equivalent or 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction, and the like.

The presence of hydrogen at the coupling site (the site on the coupler molecule at which Z is attached) provides a 4-equivalent coupler, and the presence of a coupling-off group other than hydrogen usually provides a 2-equivalent coupler. Representative classes of such coupling-off groups include, for example, chloro, alkoxy, aryloxy, heterocyclyloxy, sulfonyloxy, acyloxy, acyl, heterocyclyl, sulfonamido, heterocyclylthio, benzothiazolyl, phosphonyloxy, alkylthio, arylthio, and arylazo. These coupling-off groups are described in the art, for example, in U.S. Pat. Nos. 2,455,169, 3,227,551, 3,432,521, 3,467,563, 3,617,291, 3,880,661, 4,052,212, and 4,134,766; and in U.K. Patents and published applications 1,466,728, 1,531,927, 1,533,039, 2,066,755A, and 2,017,704A, the disclosures of which are incorporated herein by reference. Halogen, alkoxy and aryloxy groups are most suitable.

Examples of specific coupling-off groups are —Cl, —F, —Br, —SCN, —OCH$_3$, —OC$_6$H$_5$, —OCH$_2$C(=O)NHCH$_2$CH$_2$OH, —OCH$_2$C(O)NHCH$_2$CH$_2$OCH$_3$, —OCH$_2$C(O)NHCH$_2$CH$_2$OC(=O)OCH$_3$, —P(=O)(OC$_2$H$_5$)$_2$, —SCH$_2$CH$_2$COOH, In a preferred embodiment, the coupler of the invention is described by formula (Ia),

$$\text{(Ia)}$$

[Structure showing formula (Ia) with OH, X, Z, R$_3$ on phenol ring, NHCO—C(R$_4$)(R$_5$)—SO$_2$— linking to phenyl ring with (R$_7$)$_m$]

In formula (Ia), R$_3$, R$_4$, R$_5$, X and Z are as described above for formula (I). Each R$_7$ independently represents a linear or branched, saturated or unsaturated alkyl group such as methyl, t-butyl, t-pentyl, t-octyl, dodecyl, pentadecyl, octadecyl or a perfluoroalkyl group such as trifluoromethyl or heptafluoropropyl; a hydroxy group; an alkoxy group such as methoxy, t-butoxy or tetradecyloxy; an aryloxy group such as phenoxy, 4-t-butylphenoxy or 4-dodecylphenoxy; an alkyl or aryl acyloxy group such as acetoxy or dodecanoyloxy; an acylamino group such as acetamido, benzamido, or hexadecanamido; a sulfonyloxy group such as methylsulfonyloxy, dodecylsulfonyloxy, or 4-methylphenylsulfonyloxy; a sulfamoylamino group such as N-butylsulfamoylamino, or N-4-t-butylphenylsulfamoylamino; a sulfonamido group such as methanesulfonamido, 4-chlorophenylsulfonamido or hexadecanesulfonamido; a ureido group such as methylureido or phenylureido; an alkoxycarbonyl or aryloxycarbonylamino group such as methoxycarbonylamino or phenoxycarbonylamo; a carbamoyl group such as N-butylcarbamoyl or N-methyl-N-dodecylcarbamoyl. "m" represents an integer of 0 to 5, and if m is more than 1 then the substituents R$_7$ may be the same or different.

Most preferably, in formula (Ia), R$_4$, R$_5$ and (R$_7$)$_m$, contain a total of 8 to 30 carbon atoms.

In another preferred embodiment, the coupler of the invention is described by formula (Ib), wherein $R_3$, $R_4$, $R_5$, X and Z are as described above for formula (I), and $R_8$ represents a linear, branched or unbranched, cyclic or acyclic, saturated or unsaturated alkyl group such as methyl, isopropyl, hexyl, dodecyl, octadecyl, cyclopropyl or cyclohexyl group. Preferably, $R_4$, $R_5$, and $R_8$ contain a total of 8 to 30 carbon atoms.

It is essential that the substituent groups in formulas (I), (Ia), and (Ib) be selected so as to adequately ballast the coupler and the resulting dye in the organic solvent in which the coupler is dispersed. The ballasting may be accomplished by providing hydrophobic substituent groups in one or more of the substituent groups. Generally a ballast group is an organic radical of such size and configuration as to confer on the coupler molecule sufficient bulk and aqueous insolubility as to render the coupler substantially nondiffusible from the layer in which it is coated in a photographic element. Suitable ballasting may also be accomplished by providing a plurality of groups which in combination meet these criteria. Thus the combination of substituent groups in formula (I) are suitably chosen to meet these criteria. To be effective, the ballast must contain at least 8 carbon atoms. Furthermore, even if the coupling-off group Z contains a ballast, it is usually necessary to ballast the other substituents as well, since Z is eliminated from the molecule upon coupling; thus, the ballast is most advantageously provided as part of groups $R_4$, $R_5$, and $R_6$, $R_7$, or $R_8$, as appropriate.

The following cyan dye-forming couplers further illustrate the invention.

Unless otherwise specifically stated, "substituents" or substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1994, Item 36544, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. Certain desirable photographic elements and processing steps, particularly those useful in conjunction with color reflective prints, are described in *Research Disclosure*, Item 37038, February 1995.

Besides the couplers of the invention, other cyan image dye-forming couplers may be included in the element such as couplers described in the patents and publications described in the background. Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine Literature Ubersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3- position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Pat. 1,530,272; and Japanese Application 58-113935. The masking couplers may be shifted or blocked, if desired.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the compositions may be blocked or coated in protected form as described, for example, in Japanese Application 61/258,249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent No. Publications: 272,573; 335,319; 336,411; 346,899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C.R. Bart, J.R. Thirtle and P.W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and $-SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, $-COOR_V$ and $-NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group, which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. No. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

wherein IN is the inhibitor moiety, Z is selected from the group consisting of nitro, cyano, alkylsulfonyl; sulfamoyl

(—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,33 90-079,690; 90-079, 691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. One type of element is designed for image capture. In such an element, speed (the sensitivity of the element to light) is critical to obtaining sufficient image. Such elements may also include masking couplers and other information components since the element is not for direct viewing. These described elements are typically processed in the known Kodak C-41 color process as described in The British Journal of Photography Annual of 1988, pages 191–198. Such negative working emulsions are typically sold with instructions to process using a color negative method such as the mentioned C-41 process.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamido-ethyl)aniline sesquisulfate hydrate, 4-amino-3-methyl-N-ethyl-N-(2-hydroxyethyl)aniline sulfate, 4-amino-3-(2-methanesulfonamido-ethyl)-N,N-diethylaniline hydrochloride and

4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

Synthesis Example

The cyan coupler of this invention can be prepared by reacting an alkyl or aryl acid chloride with an appropriate aminophenol, such as 2-amino-5-ethyl-4,6-dichlorophenol to form the sulfone-containing 2-acylamino cyan coupler. The synthesis of cyan coupler M-2 will further illustrate the invention.

Preparation of Sulfone-Containing Ballast Acid Chloride

A solution of 100 g (0.05 mol) methyl α-bromotetradecanoate (2) 160.5 g (0.05 mol) sodium benzene sulfinate (1) in 1000 ml THF and 100 ml methanol was refluxed overnight. The solvent was removed under reduced pressure. The residual product was treated with $CH_2Cl_2$. The insoluble materials were filtered off and discarded. The filtrate was mixed with an equal volume of ligroin and passed through a silica gel pad. The solvent was then removed under reduced pressure to give 155 g (81%) of crystalline white solid product (3).

The sulfone ballast ester (3) was dissolved in 750 ml THF and 375 ml methanol and treated with a solution of 80 g NaOH in 300 ml water. After stirring at room temperature for 1 hour, the mixture was poured into a cold solution of HCl. The white solid which precipitated out was collected, washed with water and dried to give 143 g (96%) of the pure white solid product (4); m.p. 81°–83° C.

To a solution of 9.2 g (0.025 mol) of the sulfone ballast acid (4) in 100 ml $CH_2Cl_2$ was added with stirring 9.5 g (0.075 mol) oxalyl chloride and 3 drops of DMF. After stirring at room temperature for 2 hours, the mixture was concentrated under reduced pressure to give 9.6 g of the sulfone ballast acid chloride (5) as an oil.

Preparation of Cyan Coupler M-2

To a stirred suspension of 9.5 g (0.025 mol) 2-amino-5-ethyl-4,6-dichlorophenol p-toluenesulfonic acid salt (6) in 150 ml THF was added 9.1 g (0.075 mol) N,N-dimethylaniline and 9.6 g (0.025 mol) of the sulfone ballast acid chloride (5) prepared as described above. After stirring at room temperature for 2 hours the reaction mixture was poured into ice water containing 10 ml concentrated HCl. The oil which separated was extracted with $CH_2Cl_2$ and chromatographed through a silica gel column, eluting with $CH_2Cl_2$:EtOAc (9:1, v:v). The fractions containing the pure product were combined and the solvent was removed under reduced pressure to give a colorless oil. Upon standing at room temperature overnight the oil solidified to give 10.4 g (75%) of product whose structure corresponds to cyan coupler M-2; m.p. 86°–87° C.

Calcd. for $C_{28}H_{39}Cl_2NO_4S$: C, 60.42; H, 7.06; N, 2.52

Found: C, 60.47; H, 6.99; N, 2.45

Photographic Examples

Preparation of Photographic Elements 101–108

On a cellulose acetate-butyrate support were coated the following layers:

First Layer

An emulsion layer comprising (per square meter) 3.77 grams gelatin, an amount of silver bromoiodide emulsion containing the amount of silver (in grams) indicated in Table 1, $1.61 \times 10^{-3}$ mole of the coupler indicated in Table 1, and an amount of the coupler solvent dibutyl phthalate equal to the weight of coupler. It was noted during preparation of the coating compositions that comparison coupler C-1 was much more difficult to dissolve than the other couplers.

Second Layer

A protective layer containing 2.69 grams gelatin and 0.12 gram bis(vinylsulfonyl)methane per square meter.

TABLE 1

| Comparison or Invention | Element | Coupler | Silver |
|---|---|---|---|
| Comparison | 101 | C-1 | 0.90 |
| Comparison | 102 | C-2 | 0.45 |
| Comparison | 103 | C-3 | 0.45 |
| Comparison | 104 | C-4 | 0.45 |
| Comparison | 105 | M-1 | 0.45 |
| Comparison | 106 | M-2 | 0.45 |
| Comparison | 107 | M-3 | 0.45 |
| Comparison | 108 | M-4 | 0.45 |

The comparison couplers used were:

C-1

C2

C-3

(C-4)

Comparison coupler C-1 is a cyan coupler widely used in color negative films throughout the photographic industry. Comparison couplers C-2, C-3 and C-4 are typical of cyan couplers used in color photographic papers and color print films. They are closely related to the couplers of the invention, except that they have an oxygen atom (—O—) instead of the sulfonyl group(—$SO_2$—). Comparison coupler C-3 in particular is a cyan coupler widely used in color photographic papers.

The coupler solvent dibutyl phthalate is one widely used with cyan couplers in both films and papers.

Preparation of Processed Photographic Examples 201–208

Processed film samples 201–208 were prepared by exposing photographic elements 101–108 through a step wedge and processing as follows:

| Process Step | Time (min.) | Temp. °C. |
|---|---|---|
| Developer | 2.75 | 37.8 |
| Stop Bath | 0.30 | 37.8 |
| Bleach | 4.00 | 37.8 |
| Water wash | 3.00 | 37.8 |
| Fixer | 4.00 | 37.8 |
| Water wash | 3.00 | 37.8 |

The processing solutions used in the above process had the following compositions (amounts per liter of solution):

| Developer | |
|---|---|
| Potassium carbonate | 37.50 g |
| Sodium sulfite | 4.00 g |
| Potassium iodide | 1.20 mg |
| Sodium bromide | 1.30 g |
| 1,3-Diamino-2-propanoltetraacetic acid | 2.50 g |
| Hydroxylamine sulfate | 2.00 g |
| Developing agent Dev-1 | 4.50 g |
| pH adjusted to 10.00 at 26.7° C. | |
| Stop bath | |
| Sulfuric acid | 10.00 g |
| Bleach | |
| Ammonium bromide | 150.00 g |
| Ammonium ferric ethylenediaminetetra acetate | 77.00 g |
| Ethylenediaminetetraacetic acid | 6.13 g |
| Acetic acid | 9.50 mL |
| Sodium nitrate | 35.00 g |
| pH adjusted to 6.00 at 26.7° C. | |
| Fixer | |
| Ammonium thiosulfate | 91.53 g |
| Ammonium sulfite | 6.48 g |
| Sodium metabisulfite | 1.00 g |
| pH adjusted to 6.50 at 26.7° C. | |

Dev-1

The spectra of the resulting dyes were measured and normalized to a maximum absorption of 1.00. The wavelengths of maximum absorption were recorded as "λmax," and are shown in Table 2. As a measure of the sharpness of the cut on the left (short wavelength) side of the absorption band, the "left bandwidth" (LBW) was obtained by substracting from the λmax wavelength at the point on the left side of the absorption band where the normalized density is 0.50 or one half the density at λmax. A lower value of LBW indicates a narrower absorption band and a reduction in unwanted green absorption. The LBW values are shown in Table 3.

TABLE 2

| Comparison or Invention | Example | Element | Coupler | λmax |
|---|---|---|---|---|
| Comparison | 201 | 101 | C-1 | 694 |
| Comparison | 202 | 102 | C-2 | 668 |
| Comparison | 203 | 103 | C-3 | 668 |
| Comparison | 204 | 104 | C-4 | 668 |
| Invention | 205 | 105 | M-1 | 682 |
| Invention | 206 | 106 | M-2 | 690 |
| Invention | 207 | 107 | M-3 | 691 |
| Invention | 208 | 108 | M-4 | 687 |

TABLE 3

| Comparison or Invention | Example | Element | Coupler | LBW |
|---|---|---|---|---|
| Comparison | 201 | 101 | C-1 | 84 |
| Invention | 205 | 105 | M-1 | 71 |
| Invention | 206 | 106 | M-2 | 71 |
| Invention | 207 | 107 | M-3 | 68 |
| Invention | 208 | 108 | M-4 | 71 |

The data in Table 2 show that the couplers of the invention provided image dyes whose absorption spectra were in the desired range for color negative film applications, that is, longer than 680 nm, whereas the comparison couplers that have an oxygen atom (—O—) instead of the sulfonyl group(—$SO_2$—) of the invention (C-2, C-3, C-4) yielded image dyes whose absorption spectra were much shorter than 680 nm.

The data in Table 3 show that the couplers of the invention provide image dyes with desirably low side absorptions on the short wavelength side of the absorption band, as evidenced by their low values of LBW, whereas the dye from comparison coupler C-1 has much more unwanted absorption on the short wavelength side.

Figure 1:
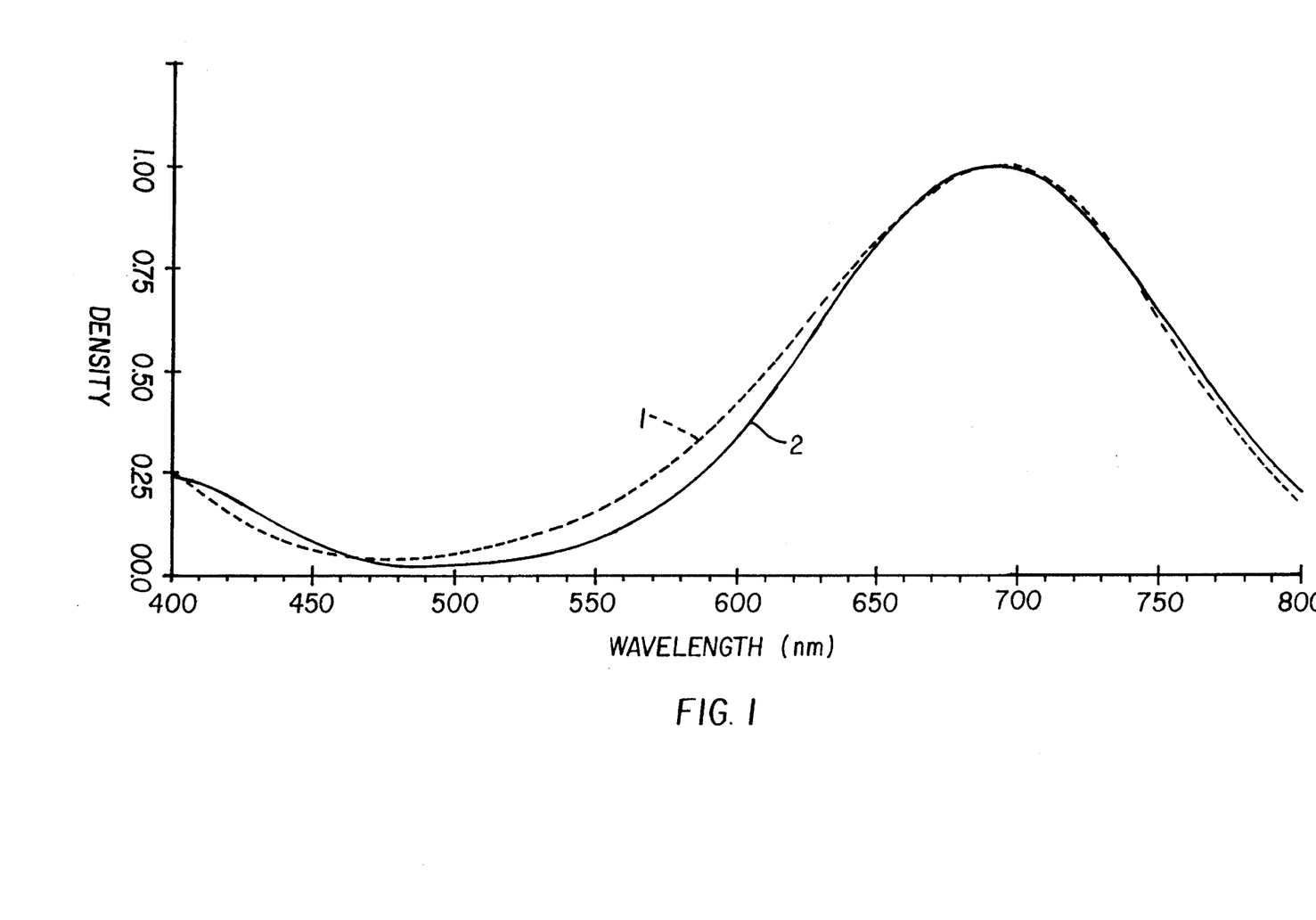
FIG. 1 is an absorption spectra of image dyes in Processed Photographic Example 201 (Coupler C-1, broken line) and Example 206 (Coupler M-2, solid line) which shows the lower unwanted green and blue absorption of the inventive element.

The dye hue advantages of the couplers of the invention are further illustrated by the absorption spectra shown in FIG. 1, which compares the dye hues of coupler M-2 of the invention (solid line 2) with comparison coupler C-1 (broken line 1), a coupler now widely used in color negative films. It is clear that the dye from coupler M-2 has much less unwanted green absorption than the dye from coupler C-1.

Furthermore, the couplers of the invention were easily and economically prepared, dissolved readily in coupler solvent, and provided photographic elements of excellent quality and stability, whereas comparison coupler C-1 was difficult to dissolve in coupler solvent, and is an expensive coupler to manufacture.

The entire contents of the various patent applications, patents and other publications referred to in this specification are incorporated herein by reference.

What is claimed is:

1. A photographic element comprising a light sensitive silver halide emulsion layer having associated therewith a cyan coupler as represented by formula (I):

wherein:

$R_3$ represents an alkyl group of 2 to 15 carbon atoms;

$R_4$ and $R_5$ each independently represents a hydrogen atom, an alkyl group or an aryl group;

$R_6$ represents an alkyl or aryl group;

X represents a halogen atom; and

Z represents a hydrogen atom or a group capable of being split off by oxidized color developer.

2. The element of claim 1 wherein $R_3$ contains from 2 to 4 carbon atoms.

3. The element of claim 1 wherein $R_6$ is an alkyl group having up to 20 carbon atoms.

4. The element of claim 1 wherein $R_6$ is an aryl group containing up to 30 carbon atoms.

5. The element of claim 4 wherein the aryl group is a phenyl group.

6. The element of claim 5 wherein the phenyl group bears a substituent.

7. The element of claim 1 wherein $R_4$ and $R_5$ together contain from 1 to 30 carbon atoms.

8. The element of claim 1 wherein the coupler of formula (I) is in a silver halide emulsion layer sensitive to red light.

9. A process for forming an image in an element as described in claim 1 after the element has been imagewise exposed to light comprising contacting the exposed image with a color developing agent.

10. The element of claim 1 further comprising a transparent support.

11. The element of claim 1 wherein the wavelength of maximum absorption of the dye formed upon development with a p-phenylenediamine developer is at least 680 nm.

12. The element of claim 1 wherein the wavelength of maximum absorption of the dye formed upon development with a 4-amino-3-methyl-N-ethyl-N-(2-hydroxyethyl)aniline sulfate, developer is at least 680 nm.

13. A color negative element comprising a transparent support bearing a light sensitive silver halide emulsion layer having associated therewith a cyan coupler represented by formula (I):

wherein:

$R_3$ represents an alkyl group of 2 to 15 carbon atoms;

$R_4$ and $R_5$ each independently represents a hydrogen atom, an alkyl group or an aryl group;

$R_6$ represents an alkyl or aryl group;

X represents a halogen atom; and

Z represents a hydrogen atom or a group capable of being split off by oxidized color developer.

14. A light sensitive silver halide emulsion layer having associated therewith a cyan coupler represented by formula (Ia):

wherein:

$R_3$ represents an alkyl group of 2 to 15 carbon atoms;

$R_4$ and $R_5$ each independently represents a hydrogen atom, an alkyl group or an aryl group;

each $R_7$ independently represents an alkyl group; a hydroxy group; an alkoxy group; an aryloxy group; an acyloxy group; an acylamino group; a sulfonyloxy group; a sulfamoylamino group; a sulfonamido group; a ureido group; an oxycarbonyl group, an oxycarbonylamino group; or a carbamoyl group where m is 0 to 5;

X represents a halogen atom; and

Z represents a hydrogen atom or a group capable of being split off by oxidized color developer.

15. A light sensitive silver halide emulsion layer having associated therewith a cyan coupler represented by formula (Ib):

wherein:

$R_3$ represents an alkyl group of 2 to 15 carbon atoms;

$R_4$ and $R_5$ each independently represents a hydrogen atom, an alkyl group or an aryl group;

$R_8$ represents an alkyl group

X represents a halogen atom; and

Z represents a hydrogen atom or a group capable of being split off by oxidized color developer.

* * * * *